United States Patent [19]

Petelenz et al.

[11] Patent Number: 4,915,685

[45] Date of Patent: Apr. 10, 1990

[54] METHODS AND APPARATUS FOR IONTOPHORESIS APPLICATION OF MEDICAMENTS AT A CONTROLLED PH THROUGH ION EXCHANGE

[76] Inventors: Tomasz J. Petelenz, 623 University Village, Salt Lake City, Utah 84108; Stephen C. Jacobsen, 274 S. 1200 East, Salt Lake City, Utah 84102; Robert L. Stephen, 2501 Kensington Ave.; Jiri Janata, 2231 Logan Ave., both of Salt Lake City, Utah 84108

[21] Appl. No.: 64,769

[22] Filed: Jun. 19, 1987

Related U.S. Application Data

[63] Continuation-in-part of Ser. No. 841,329, Mar. 19, 1986.

[51] Int. Cl.⁴ .............................................. A61N 1/30
[52] U.S. Cl. .................................................... 604/20
[58] Field of Search ................... 604/20, 21; 128/783, 128/798, 799, 802, 803

[56] References Cited

U.S. PATENT DOCUMENTS

| | | | |
|---|---|---|---|
| 3,991,755 | 11/1976 | Vernon et al. | 128/172.1 |
| 4,141,359 | 2/1979 | Jacobsen et al. | 128/172.1 |
| 4,166,457 | 9/1979 | Jacobsen et al. | 128/639 |
| 4,215,696 | 8/1980 | Bremer et al. | 128/641 |
| 4,250,878 | 2/1981 | Jacobsen et al. | 128/207.21 |
| 4,271,189 | 6/1981 | Durlach | 514/578 |
| 4,292,968 | 10/1981 | Ellis | 128/207.21 |
| 4,383,529 | 5/1983 | Webster | 604/20 |
| 4,414,842 | 11/1983 | Small et al. | 73/61.16 |
| 4,416,274 | 11/1983 | Jacobsen et al. | 604/20 |
| 4,419,092 | 12/1983 | Jacobsen et al. | 604/20 |
| 4,465,074 | 8/1984 | Buchalter | 128/639 |
| 4,474,570 | 10/1984 | Ariura et al. | 604/20 |
| 4,477,971 | 10/1984 | Jacobsen et al. | 29/877 |
| 4,526,176 | 7/1985 | Bremer et al. | 128/641 |
| 4,557,723 | 12/1985 | Sibalis | 604/20 |
| 4,570,637 | 2/1986 | Gomes et al. | 128/639 |
| 4,602,909 | 7/1986 | Csillik et al. | 604/20 |
| 4,639,244 | 1/1987 | Rizk et al. | 604/19 |
| 4,722,726 | 2/1988 | Sanderson et al. | 604/20 |
| 4,731,049 | 3/1988 | Parsi | 604/20 |

OTHER PUBLICATIONS

Molitor et al., "Studies on Iontophoresis: I. Experimental Studies on the Causes and Prevention of Iontophoretic Burns," American Journal of Medical Science, vol. 198, pp. 778–785 (Dec. 1939).

Molitor, H., "Pharmacologic Aspects of Drug Administration by Ion-Transfer," The Merck Report, pp. 22–29 (Jan. 1943).

Abramowitz, "Ion Transfer or Iontophoresis," Galvanic Current, pp. 120–124.

(List continued on next page.)

*Primary Examiner*—C. Fred Rosenbaum
*Attorney, Agent, or Firm*—Workman, Nydegger & Jensen

[57] ABSTRACT

Methods and apparatus for administering known quantities of medicaments by iontophoresis, while avoiding burns caused by extremes in the pH of the medicament medium during passage of an electric current, are disclosed. It is known that as iontophoresis progresses in conventional iontophoresis systems, the electrolysis of water occurs to produce hydrogen or hydroxyl ions at the interface of the electrode and medicament medium. Since these ions are highly mobile, they are transported directly into the skin of a patient in preference to the larger medicament ions. Thus, extreme changes in pH are experienced which result in burns due to the acidificaion or alkalinization of the medicament medium and passage of electric current through the skin. In addition, the efficiency of iontophoresis decreases over time. The present invention avoids extremes in pH by removing the hydrogen or hydroxyl ions which are created during iontophoresis and creates conditions for constant delivery over prolonged periods of time.

In the present invention, the medicament ions are attached to an ion exchange matrix, such as an ion exchange resin. When the medicament leaves the ion exchange matrix, the vacated active site is filled by the produced electrolysis products, thereby allowing iontophoresis to progress at a relatively constant pH.

14 Claims, 3 Drawing Sheets

OTHER PUBLICATIONS

Waud, D., "Iontophoretic Application of Drugs," Journal of Applied Physiology, vol. 23, pp. 128–130 (Jul. 1967).

Boone, D., "Hyaluronidase Iontophoresis," Physical Therapy, vol. 49, pp. 139–145 (1968).

Gore et al., "A Capacitive-Discharge, Microiontophoretic Device With Single-Ended Output," Journal of Applied Physiology, vol. 30, pp. 264–267 (Feb., 1971).

Spencer, H., "Programmable Nanoampere Constant Current Sources for Iontophoresis," Medical and Biological Engineering, vol. 9, pp. 693–702 (Nov. 1971).

Handbook of physical Medicine and Rehabilitation, Second Edition, Krusen et al., editors, pp. 379–380 (1971).

Geller et al., "An Improved Constant Current Source for Microiontophoretic Drug Application Studies," Electroencephalography and Clinical Neurophysiology, vol. 33, pp. 430–432 (1972).

Bloom, F. E., "To Spritz or Not to Spritz: The Doubtful Value of Aimless Iontophoresis," Life Sciences, vol. 14, pp. 1819–1834.

Kahn, J., "Acetic Acid Iontophoresis for Calcium Deposits," Physical Therapy, vol. 57, pp. 658–659 (Jun. 1977).

Johnson et al., "On the Safe Electrical Administration of Ionized Drugs/Iontophoresis," 30th ACEMB, Los Angeles, California, (Nov. 5–9, 1977).

"Painless Anesthesia Device Developed by U Researchers," Health Sciences Report, p. 5 (Jan. 1978).

Langley, "Iontophoresis to Aid in Releasing Tendon Adhesions," Physical Therapy, vol. 64, No. 9, p. 1395 (Sep. 1984).

Shaya et al., "Percutaneous Electrophoresis of Amino Acids and Urea," Medical and Biological Engineering and Computing, vol. 16, pp. 126–134 (1978).

"Iontophoresis," Medical Electronics, pp. 174 and 175 (Feb. 1984).

METHODS AND APPARATUS FOR IONTOPHORESIS APPLICATION OF MEDICAMENTS AT A CONTROLLED PH THROUGH ION EXCHANGE

RELATED APPLICATION

This application is a continuation-in-part application of our copending application, Ser. No. 841,329, filed Mar. 19, 1986, entitled METHODS AND APPARATUS FOR IONTOPHORESIS APPLICATION OF MEDICAMENTS, which application is incorporated herein by this reference.

BACKGROUND

THE FIELD OF THE INVENTION

This invention relates to methods and apparatus for administering substances by iontophoresis. More particularly, the present invention discloses methods and apparatus for administering determinable quantities of medicaments and the like by iontophoresis in a safe and efficient manner using ion exchange.

THE BACKGROUND OF THE INVENTION

The process of iontophoresis was reported as early as about 1740 for use in applying medication locally through a patient's skin and later in about 1900 for use in delivering medicaments to the eyes and ears as well. In its simplest terms, this technique involves the application of an electromotive force to drive ionic chemicals through the skin so that they can be absorbed by the adjacent tissues and blood vessels. By iontophoretic techniques, various substances (including some pharmaceuticals and medicaments) have been administered to a patient without the necessity of a hypodermic injection and without the associated problems, such as pain, the risk of infection, and trauma to the patient.

While iontophoresis ha been the subject of continuous experimentation for many years, the process has not been used to any major extent by medical practitioners. Iontophoresis has been tested for use in treatments such as the application of local anesthetics, the application of medication for treatment of skin disorders, and the application of other limited types of medications in order to achieve a localized effect.

As mentioned above, iontophoresis involves the application of an electromotive force to drive ions through the skin. Accordingly, ions bearing a positive charge are driven into the skin at the anode of an electrical system, and ions bearing a negative charge are driven into the skin at the cathode of the electrical system. For example, positively charged ions such as zinc, copper, alkaloids, certain anesthetics, and certain vasodilating drugs are introduced into the skin or the mucous membranes from the positive pole. On the other hand, a negatively charged drug, such as salicylate, fluoride, penicillin, and insulin can be driven into the skin using the negative pole.

Some drugs have exhibited their effect at the site of iontophoresis, where they are initially introduced through the skin. Examples of such drugs which exhibit localized effects upon iontophoresis through the skin are local anesthetics.

Various other drugs can be administered to exhibit systemic effects by iontophoretically driving the drug into the circulatory system. In such cases, the ions transferred through the skin are absorbed into the blood stream and enter the body's general blood circulatory system.

Iontophoretic delivery of medicaments can provide significant benefits over other methods of delivery. For example, when a medicament is taken orally, it must be absorbed through the digestive tract. However, uptake of the medicament through the digestive tract varies greatly from individual to individual. Moreover, the drug must pass through the liver where it is not unusual for upwards of 70% of the drug to be inactivated on the first pass through the liver.

Thus, because a medicament delivered iontophoretically can be quickly absorbed into the circulatory system, iontophoresis is capable of avoiding the "first pass effect" in the administration of certain medicaments. In addition, patient discomfort and noncompliance, and the risk of infection associated with injections are also eliminated when using iontophoresis.

While iontophoresis has been applied to many different drugs, it has never established itself as a widely used method for the delivery of medicaments. This was partly caused by the use of poor equipment and the lack of understanding of the mechanism of iontophoresis and its potential safety hazards. This historic view of iontophoresis, however, began to change somewhat in about 1959.

At that time, a test was devised, using iontophoresis, to diagnose cystic fibrosis It was found that pilocarpine could be iontophoretically administered onto localized areas of skin so as to induce sweating. The sweat could then be collected and tested for abnormal levels of sodium or chloride, which is diagnostic of cystic fibrosis. This technique met with approval and was eventually selected by the Cystic Fibrosis Foundation as the standard and only acceptable test for diagnosing cystic fibrosis.

The widespread use of iontophoresis in diagnosing cystic fibrosis has resulted in some noticeable improvements in the equipment used to supply electrical current and in the electrodes used in iontophoretic applications. This use of iontophoresis has also led to some additional understanding of the mechanisms involved in iontophoresis. However, outside the field of cystic fibrosis diagnosis, the technique has yet to receive widespread acceptance.

Notwithstanding the limited acceptance of iontophoresis, the potential uses of iontophoresis can be readily appreciated from the previous discussion. Iontophoresis can obviously be used to introduce medicaments and other substances into the body without the necessity of an injection. Its use could thus become extremely significant in administering drugs and pharmaceuticals where frequent injections are required.

Specifically, the primary application of iontophoresis has been for administration of locally acting medications, i.e., resulting in negligible systemic concentration and thus greatly reduced toxicity It has been acknowledged, that electrochemical reactions occurring at the electrodes cause adverse reaction of the skin and preclude extended application time required to achieve prolonged systemic effects.

Frequent injections over a prolonged period of time as a form of treatment has several disadvantages. Many individuals find it difficult to adjust to the requirement of multiple daily injections, which are painful, carry the risk of infection, and cause additional strain on their already taxed system, possibly modifying the effects of the drug.

Iontophoresis as an alternative to existing methods of systemic administration of medicaments has several advantages. The use of iontophoresis to administer such substances results in a high percentage of the substance actually reaching the systemic circulation—this is in direct contrast to oral administration where the drug is subject to the irregularities of the digestive process and possible inactivation by the liver prior to being absorbed into the systemic circulatory system. As a result, a relatively large quantity of a drug must be ingested orally in order to obtain the desired concentration of the drug in the bloodstream and to achieve the desired therapeutic effect. It will be appreciated that since each patient's digestive system functions differently, the amount of an orally ingested drug needed to achieve the desired therapeutic effect is often difficult to predict.

Another potential advantage of iontophoresis is the ability to administer medicaments over a sustained period of time without invasion of the body. Optimally, it is often desirable to maintain a certain constant level of medicament within the patient's system, instead of periodically injecting a bolus of medicament. However, due to limitations in the presently available iontophoresis systems, this sustained delivery is not practical because of the danger of electrical and chemical burns to the patient.

While the use of iontophoresis has many potential benefits, traditional iontophoretic techniques have suffered several drawbacks such that the iontophoretic administration of medicaments has not been generally very practical. In particular, traditional techniques for iontophoresis have been considered unsafe, unpredictable, inconvenient, or uneconomical. It is for these reasons that iontophoresis has not enjoyed widespread acceptance in the medical field. Moreover, due to the short duration of administration, iontophoresis has been almost exclusively used to administer locally active medicaments.

With respect to safety, it is found that iontophoresis may result in burns to the patient s skin. These burns stem from two sources: (1) galvanic sources where the electrical current itself causes burns, and (2) chemical sources where extremes in pH (which develop during the iontophoresis process) act in conjunction with electric current to result in chemical burns.

Methods and procedures have been developed to control serious galvanic burns and other electrical hazards. For example, it has been suggested that the electrical current used in the iontophoretic process be increased slowly and that limitations be placed on the amount of current delivered.

Galvanic burns can also be minimized or reduced by keeping the current density per unit area of skin below threshold values at which burning begins. Low current densities can be achieved by attention to techniques of iontophoresis, such as avoiding folds or wrinkles between the electrode and the skin (which cause high localized current density resulting in burns), using a gel-moistened electrode pad in connection with the electrode, and moistening the skin prior to and during iontophoresis. A further suggestion in the art has been to increase the surface area of the electrode so that the current is spread over a larger area, thereby reducing current density. See U.S. Pat. No. 4,416,274 (Jacobsen et al.) entitled "Ion Mobility Limiting Iontophoretic Bioelectrode," and U.S. Pat. No. 4,477,971 (Jacobsen et al.) entitled "Iontophoretic Electrode Structure."

It is more difficult to control pH and the resulting burns caused by extremes in the alkalinity or acidity of the medicament solution during passage of electric current. As the current passes between the electrode contact and the medium containing medicament, there is increased production of hydrogen ions ($H^+$) or hydroxide ions ($OH^-$). This increase in concentration is caused by the exchange of charge through the electrolysis of water.

Since the $H^+$ and $OH^-$ which result from the electrolysis of water are significantly more mobile than most of other ions, they migrate rapidly through the solution away from the electrode and toward the skin of the patient. Thus, an area of extreme pH is ultimately created directly adjacent to the skin. This area of extreme pH is clearly dangerous and has been observed to cause serious burns when the current causes these ions to pass through the skin. Thus, the changes in pH has imposed a time limit on the duration of prior art iontophoretic treatments, usually limited to only about twenty (20) to thirty (30) minutes per treatment.

Attempts have been made to control pH in the iontophoretic system. Heretofore, these attempts have been less than satisfactory. One method of attempting to control pH has been to introduce a buffer into the iontophoretic system. The introduction of buffers, however, is found to defeat some of the important useful features of iontophoresis.

The introduction of buffers results in increasing concentrations of additional ionic species within the system. In a solution containing a mixture of ions, the quantity of a specific ion that will be moved by a given electromotive force is proportional to (a) the concentration of the ion, (b) the mobility of the ion, and (c) the valence charge on the ion.

Typically, the buffer ions which, are usually small and very mobile (such as phosphate ions, and complementary cations such as sodium), will migrate through the solution at a much faster rate than will the larger ions (such as drug molecules) which are the medicament ions to be transported through the skin of the patient by the iontophoretic process. The result is that a large percentage of buffer ions may be driven into the skin by iontophoresis instead of the desirable medicament ions. Thus, the quantity of medicament molecules driven through the skin is seriously reduced and the quantity of undesirable ions driven through the skin is increased.

Moreover, as would be expected from the foregoing, the use of buffers aggravates the problem of quantification of the amount of medicament delivered in any given iontophoretic administration. If buffer ions are forced through the skin, it will be difficult or impossible to determine how much of the medicament has passed through the skin. This is particularly true since most medicament ions, especially drug ions, are larger and therefore, slower in the electrical field created during the iontophoresis process than are the smaller buffer ions.

The existing literature has pointed out that administration of substances by ion transfer long has been regarded as one of the least accurate methods of administration. Indeed, the lack of accurate quantification techniques has been, and still is, one of the major objections to wide acceptance of iontophoresis.

A further problem encountered in the clinical use of iontophoresis is that iontophoresis systems have not been particularly convenient or economical. Generally, other methods of administration of medicaments have been less expensive and easier to use. Considerations of cost and convenience have, therefore, also impeded the general acceptance of iontophoresis.

As can be appreciated from the above discussion, the technique of iontophoresis has several major potential benefits for use in the medical area. Iontophoresis offers a technique whereby medicaments may be noninvasively introduced into the body. That is, the patient may receive a needed medication without the necessity of an injection of a bolus of medicament and without the unknowns associated with the "first pass effect" of oral administration. Moreover, iontophoresis has the potential of providing a method whereby continuous, sustained doses of medications may be administered.

Despite this potential for iontophoretic administration techniques, the present state of iontophoresis is such that it is not particularly safe, since both galvanic and pH-induced burns are common. While galvanic burns can, to a certain extent, be controlled by appropriate techniques known in the art, pH-related burns associated with the passage of electrical current through the solution remain problematic. These burns are painful and difficult to heal.

In addition, existing methods and apparatus do not provide for adequate quantification of the medicament being administered. This is caused in large measure by the $H^+$ and $OH^-$ produced during iontophoresis. These highly mobile ions compete with the larger, less mobile medicament molecules for introduction in the patient, thereby resulting in an inability to determine how much of the medicament actually reaches the patient. At the same time, iontophoresis has not traditionally been particularly economical or convenient.

Thus, what is needed in the art are techniques for iontophoretically administering medicaments and other substances to the body in such a manner that burns and other safety hazards to the patient are avoided. It would be a significant advancement to provide improved methods and apparatus for administration of a medicament using iontophoresis which would allow the amount of the medicament administered to be better quantified, controlled, and delivered for prolonged time periods (i.e., over a period of hours or even days).

It would be a further significant advancement in the art to provide such methods and apparatus for administering medicaments by iontophoresis which could operate safely without the addition of buffering ions. It would also be a significant advancement in the art if methods and apparatus could be provided for iontophoretic administration of medicaments which provided for close control of pH within the system. It would be still another advancement in the art to provide methods and apparatus for administration of medicaments using iontophoresis which are economical and convenient to use. Such methods and apparatus are disclosed and claimed herein.

BRIEF SUMMARY AND OBJECTS OF THE INVENTION

The present invention is related to methods and apparatus for safely administering known quantities of medicaments (such as drugs, pharmaceuticals, or other substances) to a patient using an iontophoretic process. Furthermore, the iontophoretic techniques of the present invention maintain safe pH levels without the addition of buffering ions and minimize the introduction into the solution of ions which compete with the ionic medicaments for transference through the skin.

The electrolysis reaction of water will occur at the positive electrode when the potential between the aqueous solution and the electrode exceeds approximately +1.23 volts versus a Standard Hydrogen Electrode (hereinafter sometimes referred to as "SHE"). Electrolysis of water occurs at the negative electrode when the potential between the aqueous solution and the electrode exceeds approximately −0.83 volts vs. SHE. The direct consequence of the electrolysis of water is strong acidification at the positive electrode and strong alkalinization at the negative electrode.

The present invention approaches the control of pH within the iontophoresis system by trapping the $H^+$ and $OH^-$ ions produced within the system. Medicament ions are introduced into the iontophoresis system while attached to an ion exchange material, such as an ion exchange resin. Essentially, the medicament is attached to a polymer matrix which comprises the resin or other ion exchange material. The polymer matrix, however, will release the medicament ions under certain circumstances in order to exchange the medicament for ions with greater affinity for the matrix. The polymer matrix is chosen such that the polymer matrix will release medicament ions in exchange for ions which are undesirable in the system and which are produced within the system (such as $H^+$ and $OH^-$ ions).

According to the chemical reactions involved, the polymer matrix, such as an ion exchange resin, is initially loaded with medicament by reacting the medicament with the active sites of the matrix. The loaded matrix is then introduced into the iontophoresis medium; in most circumstances, this medium will have an aqueous base. The iontophoresis medium is, in turn, in direct communication with the iontophoresis electrodes.

Since the matrix has a greater affinity for ions produced during iontophoresis than it does for medicament ions, an exchange reaction will occur. As $H^+$ or $OH^-$ ions are produced by the system through the electrolysis reaction, medicament ions are released from the matrix. Once a medicament ion is released by the matrix, an active site becomes available to support a produced $H^+$ or $OH^-$ ion.

Thus, the system introduces desirable medicament ions into the iontophoresis system and simultaneously clears the system of undesirable $H^+$ and $OH^-$ ions. As a result, it is possible for the system to operate for extended periods of time without encountering the extremes in pH which are encountered using existing technologies.

It is, therefore, a general object of the present invention to provide improved methods and apparatus for the use of iontophoresis which are safe and which allow the amount of the medicament introduced to a patient to be more accurately quantified.

Accordingly, it is an object of the present invention to provide improved methods and apparatus for the use of iontophoresis which provide for close control of the pH of the iontophoretic system to avoid burns caused by changes in pH concentration on or near the skin of the patient and to prolong treatment time during the iontophoresis process.

It is another object of the present invention to provide such an iontophoresis system which controls the pH of the medicament medium without the use of buffers.

Moreover, it is an object of the present invention to provide an iontophoresis system wherein competing ions are exchanged for medicament ions on the active sites of an ion exchange matrix so that the amount of the medicament administered remains proportional to the current flow.

It is also an object of the present invention to provide improved methods and apparatus for the use of iontophoresis which are simple, convenient and economical to use.

These and other objects and advantages of the invention will become more fully apparent from the following description and appended claims.

DETAILED DESCRIPTION OF THE PREFERRED EMBODIMENTS

A. The Mechanism of Iontophoresis

As discussed above, iontophoresis is found to be a promising method of introducing drugs and other similar substances into a patient. In particular, iontophoresis provides for the efficient delivery of drugs without invading the body. In the past, however, iontophoresis has not been widely accepted because of the inability to produce a system which was safe, quantifiable, economical, and convenient.

One of the most serious problems prohibiting the widespread clinical use of iontophoresis is the production of painful burns on the skin of the patient after only a short period of iontophoresis. In existing iontophoretic systems for current densities of approximately 0.5 mA/cm$^2$, changes in the skin are typically observed within the first five minutes of iontophoresis, and burns often occur when the process continues for thirty minutes or more depending on a total volume of an electrode. These burns are difficult to heal and may not be fully manifest until after the treatment has been completed.

The more difficult type of burns to eliminate are burns caused by extreme changes in pH of the iontophoresis solution, or iontophoresis medium, on or near the skin of the patient during passage of an electric current. In particular, electrical current flowing through an aqueous iontophoresis medium, which would typically be used where a medicament is being iontophoresed into a patient, produces a large quantity of H$^+$ or OH$^-$ ions.

These ions (H$^+$ or OH$^-$) move rapidly in response to the electromotive forces existing within the iontophoresis system because of their large electrophoretic mobility. Thus, when these ions are produced in the iontophoresis process, they are rapidly driven into the patient's skin causing localized extremes in pH. Such localized extremes in pH result in burns on the skin of patients.

Figure 1:
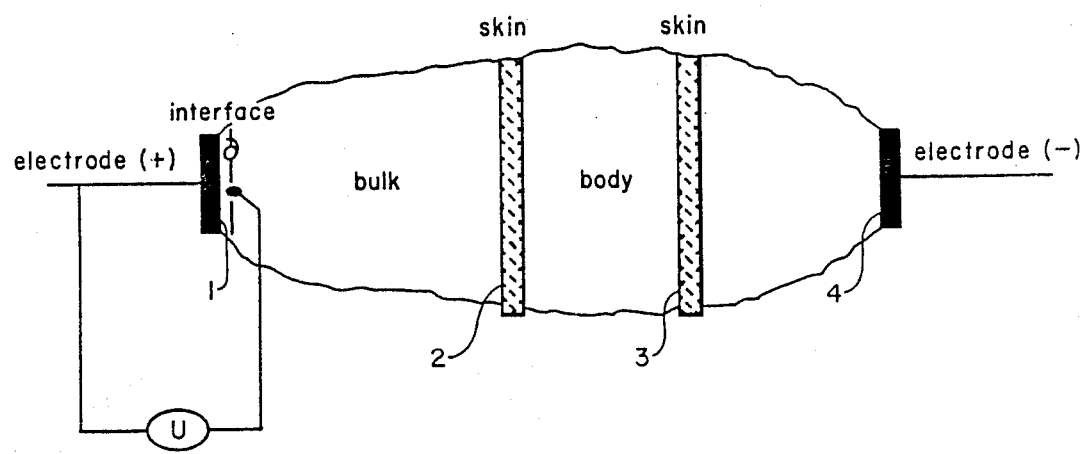
FIG. 1 is a schematic diagram of a general iontophoresis system which is within the scope of the present invention.

By definition, iontophoresis involves the transport of ions such as medicament ions, across a barrier such as the skin. The basic iontophoresis process can be clearly understood by reference to the schematic diagram of an iontophoretic system illustrated in FIG. 1. FIG. 1 illustrates the positive and negative electrode positioned on opposite sides of the body of the patient. Between the electrodes and the patient is a quantity of iontophoresis medium. By this orientation, a series of interfaces is presented.

As seen in FIG. 1, these interfaces include the electrode medium interface between the anode and the adjacent medium (generally designated at 1), the medium-skin interface (generally designated at 2) between the iontophoresis medium on the anode side of the system and the patient, a similar medium-skin interface on the cathode side (generally designated at 3), and finally the medium-cathode interface (generally designated at 4).

It will be appreciated that there will be a voltage differential across each of these interfaces, since each interface will present an additional resistance. Moreover, because for a constant current voltage is directly proportional to resistance, the additional resistance of each interface results in a greater voltage differential between the two electrodes.

However, the total voltage drop across these interfaces is not necessarily directly related to the charge transfer in the system or the amount of medicament which is transferred to the patient. As will become evident, the amount of medicament transferred depends upon both the amount of current flow and the number and characteristics of the ions which compete with the medicament ion.

The present discussion will focus on methods and apparatus for exchanging desirable medicament ions with undesirable species produced during iontophoresis.

B. The Production and Effects of H$^+$ and OH$^-$

It will be appreciated that transportation of ions takes place in an electrical field such as that produced by the system illustrated in FIG. 1. Accordingly, the medicament to be delivered to the patient must exist in the system as an ion carrying an electrical charge. Since various compounds (such as salts, bases, or acids) dissociate upon dissolution in a solvent into two components, one positive and one negative, the medicaments used in iontophoresis are in the form of ions.

Thus, one of the components in the iontophoresis solution will be an ion which is the active portion of the medicament and the other component will be either a complementary ion, or in the case of certain embodiments of the present invention, a vacated active site in an ion exchange matrix. These charged ions are then subject to the electromotive forces exerted by the electrical field during iontophoresis such that the electrical field propels the ions through the system.

During iontophoresis, the medicament ions are attracted to the electrode having the opposite charge. This transportation of ions takes place in proportion to the product of the concentration, the mobility, and the charge (or valence) of the ions in solution. The fraction of total current carried by a particular ion species which determines the amount of transported drug, is called the transference number. The transference number for an ion k is expressed by Equation (1) which follows:

$$t_k = |z_k|\mu_k C_k / \Sigma(|z_i|\mu_i C_i) \quad (1)$$

where:
- $t_k$ is the transference number of ion k,
- $z_k$ is the valence of ion k,
- $u_k$ is the mobility of ion k,
- $C_k$ is the concentration of ion k,
- i is summation index and summation is for all ions in the solution.

From Equation (1), it can be seen that as additional species are added to the system, the amount of drug, represented by ion k, transported during iontophoresis decreases for every additional species in solution. From the foregoing, it is readily apparent why the use of buffers and the like to control pH have been found to be unsatisfactory—the addition of the new species of the buffer or increase of concentration of any ion in the solution, correspondingly decrease the transport of the medicament.

In order to cause the medicament to move in the system at all, it is necessary to provide a driving force. In the case of iontophoresis, the driving force is an electrical potential difference. In order to cause current flow through the drug solution, it is necessary to provide a mechanism for charge exchange between the contact material of the electrode (typically a metal) and the electrolyte in the medium.

There are two types of electrodes which can be used for introducing a current through the iontophoresis system. These electrodes can generally be considered either "inert" or "reactive." The development of "reactive" electrodes is very new and is described in greater detail in our copending application identified above. For the purposes of the present discussion, however, an inert electrode will be presumed.

An "inert" electrode, is defined as an electrode at which the charge is exchanged with the solution according to the reaction of the electrolysis of water, as represented here at the positive pole, in Equation (2):

$$2 H_2O = O_2 + 4H^+ + 4e^- \quad (2)$$

at $V \geq 1.23$ V (at the positive pole) vs. SHE, where $e^-$ is the electron charge.

According to Equation (2), the electrolysis of water occurs if the voltage between the solution adjacent to the anode and the material of the anode exceeds approximately 1.23 volts vs. SHE. (It will be appreciated that the precise voltage for the electrolysis of water will be dependent upon the pH and the temperature of the solution, as well as certain other parameters; however, the value of approximately +1.23 volts vs. SHE is used as a typical reference value which would be encountered under typical conditions.) Thus, if the voltage at the interface of the electrode and the medicament medium exceeds the electrolysis voltage of water, $H^+$ and $OH^-$ will be formed.

The consequence of the reaction of Equation 2, as can be appreciated from the products of the reaction, is rapid acidification of the medium. The hydrogen ions produced are transported rapidly from the medium-electrode interface through the medium to the medium-skin interface, thereby resulting in acidification and contributing to burning of the skin.

While the above reaction is specific for the positively polarized electrode, it will be appreciated that a similar reaction takes place at the negative electrode where the product of the reaction is the hydroxyl ion. This reaction occurs at a voltage of approximately −0.83 volts (vs. a Standard Hydrogen Electrode) between the medium and the cathode. This, of course, creates alkalinization of the medium and tissues by the same general mechanism that acidification occurs at the positive electrode. The result, however, is the same since alkalinization can also cause burns to the patient during passage of an electric current. As can be appreciated from formula (1) transference number for any ion k decreases upon introduction of additional hydrogen or hydroxyl ions.

Also the evaluation of the transference numbers reveals that due to the introduction of $H^+$ or $OH^-$ ions into the medium during iontophoresis, the fraction of the current transported by the medicament ions does not necessarily remain constant; in fact, the amount of current transported by the medicament ions may be significantly variable over time during iontophoresis. The consequence is that the actual rate of administration of the medicament to the patient may not, and generally, will not remain constant over time.

Thus, when concentrations of $H^+$ or $OH^-$ increase there is a corresponding reduction in the amount of drug transported through the skin of the patient. The result is that the dosage of the medicament delivered cannot be accurately quantified. Moreover, the potential effective treatment time is markedly reduced because of these factors.

C. Introduction of Medicament Using An Ion Exchange Matrix

The iontophoresis system of the present invention removes produced ionic species (such as $H^+$ ions or $OH^-$ ions or buffering ions) from the iontophoresis medium, such as an aqueous solution. Since the addition of $H^+$ or $OH^-$ ions to the system is controlled, pH burns to the patient are avoided and the quantity of the medicament transported through the system remains more constant so that the amount of medicament administered is more accurately quantified, controlled, and prolonged.

The present invention removes produced ionic species from the medicament solution by introducing into the system the medicament while attached to an ion exchange matrix, such as a ion exchange resin. Ion exchange resins and related materials are generally compounds which have one or more ionizable groups bound to a hard polymer matrix. The matrix includes ions which are capable of being released in exchange for other ions which have greater affinities to the complex bound to the resin, or other type of matrix.

There are two general types of ion exchange matrices which are classified based on the type of active group and the type of exchanged ions: anion and cation exchange resins. In addition, ion exchange matrices, such as ion exchange resins may be divided into weak and strong resins, depending on the chemical functionality of the exchange group.

Usually, an ion exchange matrix, such as ion exchange resin, consists of a rigid matrix and associated active groups. One material widely used as an ion exchange matrix is a co-polymer of styrene and divinyl benzene. This copolymer is generally fabricated using suspension polymerization in an aqueous solution. The fabrication technique results in a resin in the form of small beads having tridimensional porous, rigid, and highly insoluble structures.

The degree of cross-linking within the ion exchange matrix largely determines the characteristics of the matrix. The degree of cross-linking generally varies from about 2% to about 20%, with cross-linking moderating the rigidity of the structure and the size of the pores contained within the structure. Cross-linking thus affects porosity of the resin matrix, the degree of swelling, and the rate of ionic exchange. Through control of the degree of cross-linking the various characteristics of the ion exchange resin can be carefully chosen.

As mentioned above, ion exchange materials may have varying pore sizes. The pore size may vary from dimensions comparable with the size of inorganic and small organic ions to the size allowing for easy diffusion of large organic species tens of nanometers in size. The pore size will clearly affect the characteristics of the exchange matrix, including the size of the exchanged molecules and the rate of exchange.

The exchange properties of resins are typically expressed by the exchange capacity in milliequivalents of exchange material per milligram of dry resin. This characteristic is determined mainly by the degree of cross-linking. The exchange capacity generally runs in the range of 1 to 10 milliequivalents per gram of resin in the hydrogen or chloride form. (The form of he resin is related to the ion attached to the resin structure in the process of conversion, or loading of the resin with medicament, before the reaction with the particular ion in the solution).

Another factor in the characterization of resins is the degree of swelling upon exchange of ions. The degree of swelling may vary from almost zero for so-called microreticular (i.e., "gell-like") resins, to as much as twenty-five percent (25%) for macroreticular open structure materials.

As mentioned above, the ion exchange matrix includes an active group bound to the polymer matrix. Active groups may include groups such as sulfonic acid ($-SO_3H$) for strongly acidic resins, and carboxylic groups ($-COOH$) for weekly acid cationic exchange resins. Typically, weakly acidic ion exchange resins are active at approximately a pH of 5 or less, whereas strongly acidic resins are active over a wide range of pH in both acidic and alkaline solutions.

In the case of anionic exchange resins, the active group is generally an amine. The active group may include primary, secondary, tertiary, or quaternary amines. Primary, secondary and tertiary amines provide weakly basic materials, whereas quaternary amines provide a strongly basic material.

In addition to ion exchange resins, it will be readily appreciated that other types of materials capable of performing a similar function may be used. For example, nonresinous ion exchange materials in a powdered or liquid form could be used in accordance with the present invention. Such nonresinous ion exchange material would be modified by the introduction of appropriate active groups. Examples of such nonresinous ion exchange materials are cellulose, salts of heteropolyacids, microparticulate silicas with anionic and cationic ion exchange groups.

D. Mechanism of Ion Exchange

As mentioned above, the primary goal of the present invention is to provide an iontophoresis system which provides for the elimination of undesirable electrolytic products which inevitably form at the surface of an inert electrode and which are subsequently transported to the skin of the patient. Generally, the products of the electrode reaction in iontophoresis system using an inert electrode are $H^+$ and $OH^-$, depending on the polarity of the current. These ions, however, are highly reactive in solution.

As a result, it is possible to react the hydrogen and hydroxyl ions with additional substances in the solution in order to form potentially immobile products. The consequence of such a reaction is the ability to transport a drug ion into the skin more efficiently and also to avoid pH-induced burns on the patient.

These objectives are accomplished by introducing the drug ion into the iontophoresis system while attached to an ion exchange matrix, such as an ion exchange resin. These objectives may be accomplished by two general schemes. These include the exchange of the electrolytic products for the active portion of the drug and neutralization of the electrolytic product by a complementary ion.

The ability to employ the first mechanism, drug ion exchange, is provided by the ability of ion exchange resins and the like to reciprocally take two different forms. That is, the ion exchange resin may at first be bound to a drug molecule, which is subsequently exchanged for an electrolytic product, such as an $H^+$ or $OH^-$.

The general scheme involved in the use of an ion exchange resin can generally be thought of as a two stage process. The first step involves loading the ion exchange matrix with the drug, and can be represented by Equation (3) below:

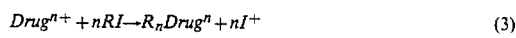
$$Drug^{n+} + nRI \rightarrow R_nDrug^n + nI^+ \qquad (3)$$

where:
R is the ion exchange matrix
I is the complementary ion
n is the valence of the drug Once the medicament has been loaded onto the ion exchange matrix, it is ready to be introduced into the iontophoresis system. Once the loaded matrix is introduced into the iontophoresis system, an exchange reaction takes place wherein the medicament is introduced into the system and the undesirable electrolytic products, such as $H^+$, become attached to the ion exchange matrix. This stage can be represented by the reaction of Equation (4):

$$R_nDrug^n + nH^{30} \rightarrow nR-H + Drug^{n+} \qquad (4)$$

Thus, it can be seen that use of the ion exchange matrix is effective in introducing medicament ions into the iontophoresis system, while clearing the system of electrolytic products that are produced during the iontophoresis process.

It will be appreciated that in order for the system to operate properly, it is necessary to design the ion exchange matrix properly. This is true because of the difficulty in achieving efficient exchange because of the very large difference in the molecular weights between the drug ion and the hydrogen and hydroxyl ions. In particular, appropriate geometry of the resin bed must be chosen in order to facilitate an acceptable transportation rate of the electrolytic products. Such geometry can be chosen as follows: a resin can be in the form of a sealed bed, or a membrane compartment containing an electrode and a compartment contacting the skin, or can be in the form of freely floating resin grains.

E. Delivery of Morphine Using an Ion Exchange Matrix Within the Scope of the Present Invention An example of use of this system is in the delivery of morphine to a patient. Generally, morphine exists in the form of morphine sulfate. Thus, the first stage, or loading reaction, of morphine sulfate into an exchange matrix will proceed according to the following Equation (5):

$$2MH^+ + SO_4^{-2} + 2RH \rightarrow 2RM + SO_4^{-2} + 4H^+ \quad (5)$$

where:
  M is morphine
  R is the ion exchange resin

In Equation (5), the morphine and sulfate ions are shown as disassociated in solution. The morphine ion is then free to become bound to the resin matrix in exchange for a hydrogen ion. It will be appreciated that in practice the exchange reaction may be conducted as a batch process with subsequent rinsing of the morphinated resin. Once the morphinated resin is recovered, it is ready for use in the iontophoresis system.

Once the morphinated resin is introduced into an iontophoresis system, the morphine can be released upon acidification of the solution. That is, once the electrolysis reaction of water begins to take place and hydrogen ions are generated, the hydrogen ions may be substituted for the morphine on the ion exchange matrix. This takes place according to the following Equation (6):

$$RM + 2H^+ \rightarrow RH + MH^+ \quad (6)$$

where:
  $MH^+$ is the charged drug.

Once the morphine is released in its active charged state, it is available for transport into the skin of the patient by the flowing current in the iontophoresis system. In practice it is desirable to provide sufficient active sites on the ion exchange resin to allow $H^+$ within the system to become attached to the resin and immobilized.

As an alternative, the ion exchange resin may be used in a counter ion exchange mechanism. Using this mechanism, the initial reaction is the conversion of the resin into a sulfated form with simultaneous release of hydroxyl ions. The hydroxyl ions are in turn neutralized by the hydrogen ions present in the solution. In order to maintain pH within proper limits, it is necessary to maintain a slight excess of the resin in the system to compensate for the lower than maximum efficiency of the exchange reaction.

Within a specific range of pH, morphine as a freebase is relatively insoluble in an aqueous solution. As a result, at pH > approximately 8.2 it generally precipitates out on the resin beads within the system. Upon the introduction of hydrogen ions due to the electrolytic reaction within the system, the pH is lowered which results in increasing solubilization of the morphine precipitate. Once the morphine is solubilized, it can be transported into the skin using the iontophoresis mechanism.

The counter ion exchange mechanism is outlined in the following Equations (7) and (8).

$$2MH^+ + SO_4^{-2} + 2ROH \rightarrow 2M_{(precip.)} + R_2^- So_4 + 2H-OH \quad (7)$$

where:
  M is morphine
  R is ion exchange resin

Solubilization occurs as follows:

$$M_{(precip.)} + H^+ \rightarrow MH^+_{(soluble)} \quad (8)$$

As a result, the solubilization of morphine base requires a 1:1 ratio between excess hydrogen ions and the amount of morphine. Thus, it is only when morphine capacity is exhausted that pH of the solution drops and the efficiency of drug transport is reduced.

Figure 2:
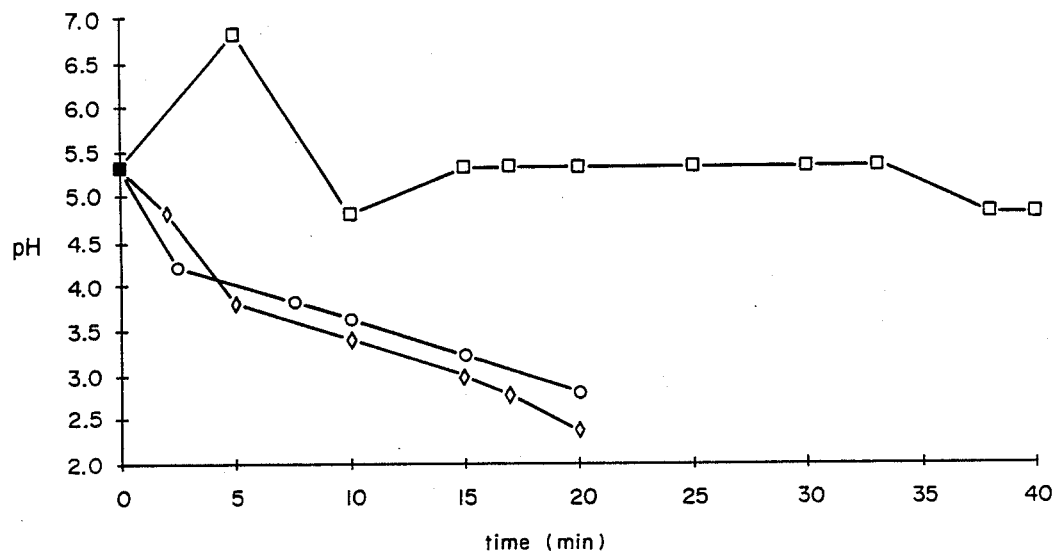
FIG. 2 is a graph showing pH in electrophoresis of morphine sulphate in-vivo with and without pH control with an ion exchange resin.

FIG. 2 illustrates the pH experienced using an ion exchange resin as described, compared to iontophoresis by conventional methods. The upper curve illustrated in FIG. 2 represents the pH encountered over approximately 40 minutes using an exchange resin. As can be seen, the pH remained relatively constant and did not dip into the dangerously lower pH levels.

The two lower curves shown in FIG. 2, conversely, illustrate pH levels using conventional techniques. It can be seen that using conventional techniques pH rapidly declines to dangerous levels and must be discontinued within 30 minutes.

Figure 3:
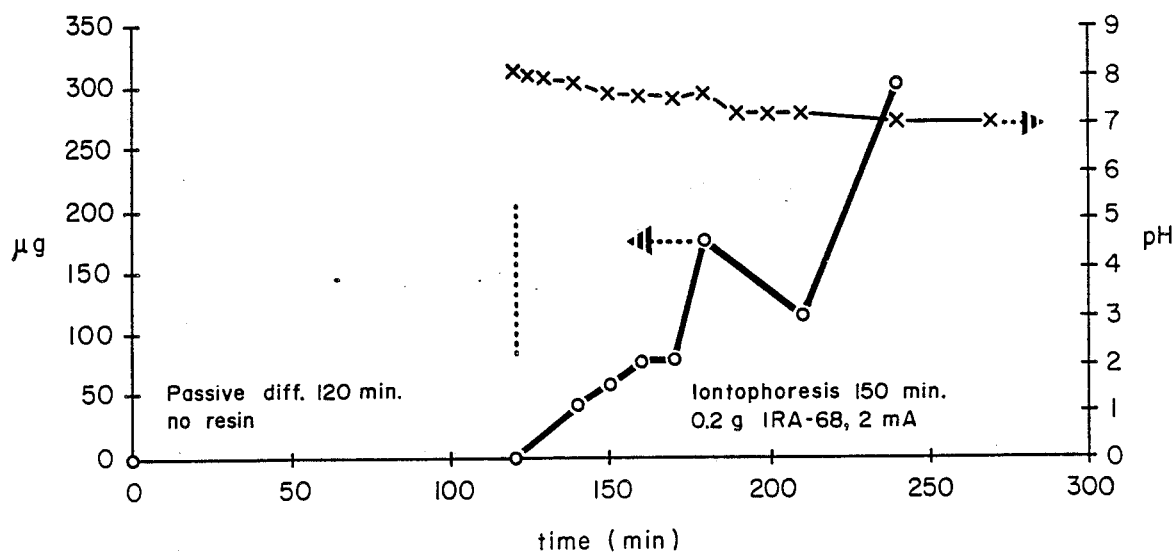
FIG. 3 is a graph depicting iontophoresis of morphine in-vitro with pH control with ion exchange resin as well as with passive infusion with no resin.

FIG. 3 illustrates the effectiveness of iontophoresis employing the ion exchange resin techniques described. It can be seen that there is no passive diffusion of morphine into the patient over the first 120 minutes of passive contact. Once iontophoresis is initiated, however, blood morphine levels rapidly increase until the experiment is terminated.

In summary, it is possible to use an ion exchange matrix in order to maintain the pH of the iontophoresis system. The ion exchange matrix allows a drug ion to be introduced into the system in exchange for undesirable produced electrolysis products. As a result, a quantifiable amount of drug can be efficiently introduced to the patient without encountering extremes in pH as is typical in using existing iontophoresis systems. Thus, the objects of the invention discussed above are accomplished. The system is able to maintain pH over time and thus, iontophoresis can be extended over a much longer period of time.

F. Examples

The following examples are given to illustrate the general scope of the present invention. These examples are not intended to limit the scope of the present invention.

EXAMPLE 1

An iontophoresis procedure within the scope of the present invention may be performed for the purpose of administering morphine to a human patient. The drug is initially obtained in the form of sulfate in an aqueous solution having a concentration of about 10 mg/ml. An ion exchange matrix is obtained in the form of $H^+$. The drug may be then loaded onto the ion exchange matrix by batch process with continuous stirring for 3-4 hours. The loaded resin is then isolated by washing with deionized water with frequent refreshing of rinsing solution for a period sufficient to eliminate excess of $SO^{-2}$.

The loaded ion exchange matrix may then introduced into an iontophoresis system. The system includes an inert electrode made out of glassy carbon. The loaded resin is introduced into the iontophoresis system into a solution of water which is placed between the electrode and the skin of the patient. The initial pH of the iontophoretic solution is about 5.5 to 6.

Current of about 2 uA is then passed through the system. After a period of approximately 60 minutes, the pH of the system is maintained at a level of about 4.5 to about 5.

The physiological reactions typically observed in the administration of morphine are demonstrated by the patient. Free drug levels measured in the serum by radioimmunio assay technique indicate an increase of the drug concentration and correlated with the time of iontophoresis.

EXAMPLE 2

An iontophoresis procedure within the scope of the present invention was performed for the purpose of administering morphine in vivo across the skin surface to a human patient. The drug was initially obtained in the form of morphine sulphate in an aqueous solution having a concentration of about 6 ug/ml. An ion exchange matrix was obtained. The drug was then loaded onto the ion exchange matrix by adding 0.2 g of a resin into a solution of morphine directly in the electrode. The electrode contact was made of glassy carbon. The loaded resin was placed between the glassy carbon electrode and the skin of the patient. The initial pH of the iontophoretic solution was about 8.

Figure 4:
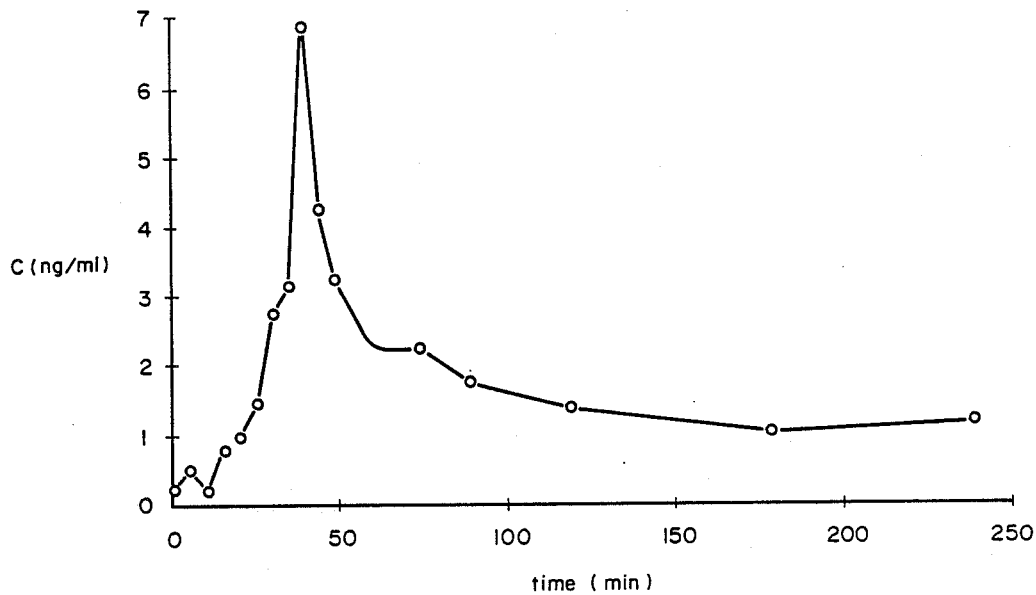
FIG. 4 is a graph depicting results for the iontophoresis of morphine in terms of morphine within the blood.

Current of about 2 mA was then passed through the system. After a period of approximately 120 minutes, the pH of the system was maintained at a level of about 7. The results of this test run are graphically illustrated in FIG. 4. FIG. 4 illustrates the concentration of morphine in the blood of the patient over time.

The physiological reactions typically observed in the administration of morphine were demonstrated by the patients.

EXAMPLE 3

An iontophoresis procedure within the scope of the present invention was performed for the purpose of administering morphine to a human patient. The drug was initially obtained in the form of morphine sulphate in an aqueous solution having a concentration of about 10 ug/ml. An ion exchange matrix was obtained in the form of JRA-68 ion exchange resin. Approximately 0.5 g of resin was placed in a cylindrical electrode having a glassy carbon contact. the electrode was then placed over the skin of a patient with resin contained between the contact and a filter paper dish, preventing a direct contact between resin grains and the skin. The initial pH of the iontophoretic solution was about 5.5.

Current of about 1.3 mA was then passed through the system. After a period of approximately 40 minutes, the pH of the system was maintained at a level of about 4.5 to about 5. The results of this run are graphically illustrated on the upper line of FIG. 2.

The physiological reactions typically observed in the administration of morphine were demonstrated by the patients. Free drug levels measured in the serum by radioimmunio assay technique indicated an increase of the drug concentration and correlated with the time of iontophoresis.

EXAMPLE 4

An iontophoresis procedure within the scope of the present invention is performed for the purpose of administering morphine to a human patient. The drug is initially obtained in the form of morphine sulphate in an aqueous solution having a concentration of about 10 ug/ml. An ion exchange matrix is obtained in the form of a carbon exchange resin The drug is then loaded onto the ion exchange matrix by mixing appropriate amounts with the resin (in slight excess of the ion exchange capacity of the resin). The loaded resin is then isolated by washing with water.

The loaded ion exchange matrix is then introduced into an iontophoresis system. The system includes an inert electrode made of glassy carbon. The loaded resin is introduced into the iontophoresis system in the form of a dish embedded in a gel is placed between the electrode and the skin of the patient.

Current having a density of about 0.5 mA/cm$^2$ is then passed through the system. The pH of the system was maintained at a constant level of about the initial pH.

The physiological reactions typically observed in the administration of morphine are demonstrated by the patients. These reactions included the histamine release and markedly reduced pain threshold. Free drug levels measured in the serum by radioimmunio assay technique indicate an increase of the drug concentration correlated with the time of iontophoresis.

EXAMPLE 5

An iontophoresis procedure within the scope of the present invention is performed for the purpose of administering morphine to a human patient. The drug is initially obtained in the form of morphine sulphate in an aqueous solution having a concentration of about 10 ug/ml. An ion exchange matrix is obtained in the form of a JRA-68 ion exchange resin. The drug is dissolved in water with approximately 30% added glycerol.

The ion exchange matrix is then introduced into an iontophoresis system. The system included an inert electrode made out of glassy carbon. The resin is introduced into the iontophoresis system into a solution of morphine which is placed between the electrode and the skin of the patient. The initial pH of the iontophoretic solution is about 8.

Current of about 2 mA was then passed through the system. After a period of approximately 60 minutes, the pH of the system is maintained at a level of about 7-8.

Figure 5:
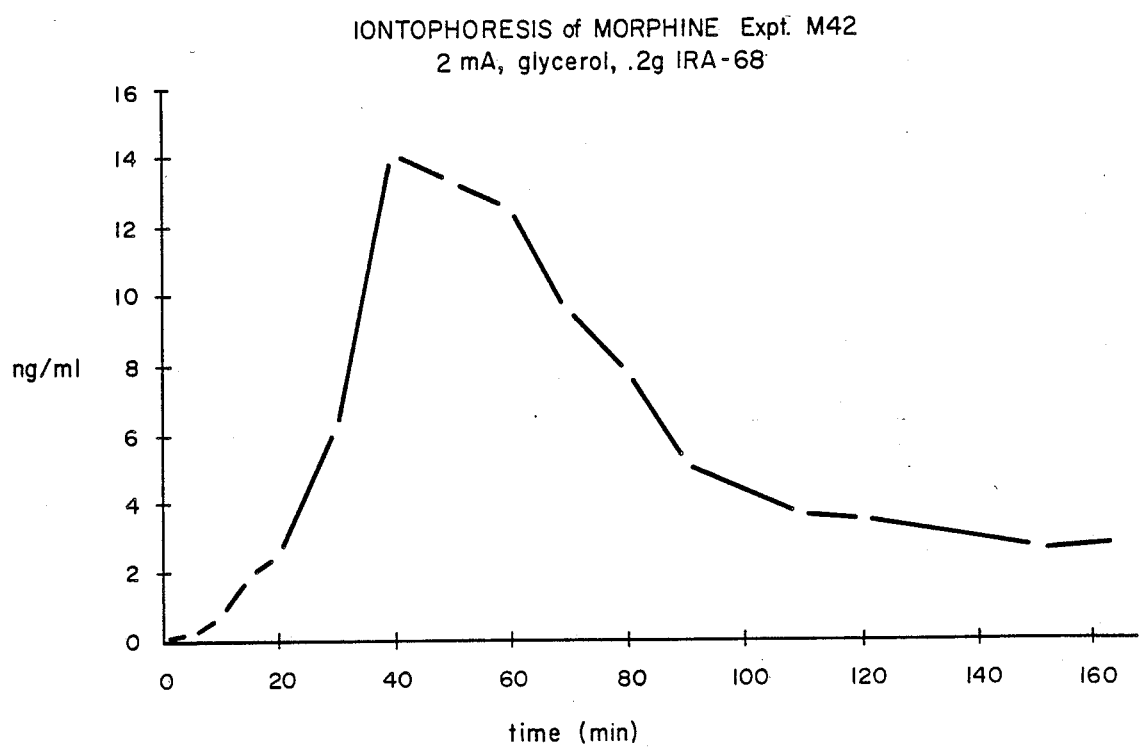
FIG. 5 is a graph depicting results for the iontophoresis of morphine in terms of morphine within the blood.

The physiological reactions typically observed in the administration of morphine are demonstrated by the patient. Free drug levels measured in the serum by radioimmunio assay technique indicated an increase of the drug concentration and correlated with the time of iontophoresis. The amounts of drug found in the blood under similar conditions are plotted in FIG. 5.

G. Summary

In summary, the present invention makes it possible to maintain pH at safe levels during the iontophoresis procedure. The use of the ion exchange matrix is desirable where competing ions produced during the procedure required removal from the system. Thus, when employing the present invention, undesirable ions produced during the process are cleared from the iontophoresis medium at the same time desirable medicament ions are introduced into the medium.

The invention may be embodied in other specific forms without departing from its spirit or essential characteristics. The described embodiments are to be considered in all respects only as illustrative and not restrictive. The invention is, therefore, indicated by the appended claims, rather than by the foregoing description. All changes which come within the meaning and range of equivalency of the claims are to be embraced within their scope.

What is claimed and desired to be secured by U.S. Letters Patent is:

1. A method for iontophoretically administering a medicament through the skin of a patient while simultaneously removing competing ions from the medicament medium, the method comprising the steps of:
   (a) obtaining an ion exchange matrix and a drug comprising medicament ions which are insoluble in an iontophoresis medium and complementary ions;
   (b) obtaining a first electrode and a second electrode;
   (c) obtaining an iontophoresis medium;
   (d) placing the ion exchange matrix and the drug in communication with iontophoresis medium such that the medicament ions are precipitated onto the ion exchange matrix;
   (e) placing the first electrode in communication with the iontophoresis medium;
   (f) placing the iontophoresis medium in communication with the patient such that the medium is disposed between the first electrode and the skin of the patient;
   (g) placing the second electrode in communication with the skin of the patient at a point distal from the first electrode; and
   (h) creating an electrical voltage difference between the first and second electrodes, said voltage difference causing the electrolysis reaction of water, the products of the electrolysis of water acting to solubilize the medicament such that the medicament ions are transported through the skin of the patient, while an approximately constant pH is maintained within the iontophoresis medium.

2. A method for iontophoretically administering a medicament as defined in claim 1 wherein the iontophoresis medium comprises an aqueous medium.

3. A method for iontophoretically administering a medicament as defined in claim 1 wherein the ion exchange matrix comprises an ion exchange resin.

4. A method for iontophoretically administering a medicament as defined in claim 3 wherein the ion exchange resin comprises a polymer.

5. A method for iontophoretically administering a medicament as defined in claim 4 wherein the ion exchange resin comprises a copolymer of styrene and divinyl benzene.

6. A method for iontophoretically administering a medicament as defined in claim 1 wherein the medicament comprises morphine.

7. A method for iontophoretically administering a medicament as defined in claim 1 wherein the medicament comprises morphine sulphate.

8. A method for iontophoretically administering medicament ions through the skin of a patient while simultaneously removing competing ions from the medicament medium the method comprising the steps of:
   (a) obtaining an iontophoresis medium;
   (b) obtaining a drug comprising medicament ions which are insoluble in the iontophoresis medium and complementary ions;
   (c) obtaining an ion exchange matrix;
   (d) reacting the drug with the ion exchange matrix such that the complementary ions become bound to the active sites of the ion exchange matrix;
   (e) obtaining a first electrode and a second electrode;
   (f) placing the drug and the ion exchange matrix in communication with the iontophoresis medium such that the medicament ions precipitate onto the ion exchange matrix;
   (g) placing the first electrode in communication with the iontophoresis medium;
   (h) placing the iontophoresis medium in communication with the patient such that the medium is disposed between the first electrode and the skin of the patient;
   (i) placing the second electrode in communication with the skin of the patient at a point distal from the first electrode; and
   (j) creating voltage difference between the first and second electrodes, said voltage difference causing the electrolysis reaction of water, the products of the electrolysis of water acting to solubilize the precipitated medicament such that the medicament ions react with the products of the electrolysis reaction of water and are then transported through the skin of the patient, while an approximately constant pH is maintained within the iontophoresis medium.

9. A method for iontophoretically administering medicament ions as defined in claim 8 wherein the iontophoresis medium comprises an aqueous medium.

10. A method for iontophoretically administering medicament ions as defined in claim 8 wherein the ion exchange matrix comprises an ion exchange resin.

11. A method for iontophoretically administering medicament ions as defined in claim 10 wherein the ion exchange resin comprises a polymer.

12. A method for iontophoretically administering medicament ions as defined in claim 10 wherein the ion exchange resin comprises a copolymer of styrene and divinyl benzene.

13. A method for iontophoretically administering medicament ions as defined in claim 8 wherein the medicament comprises morphine.

14. A method for iontophoretically administering medicament ions as defined in claim 9 wherein the medicament comprises morphine sulphate.

* * * * *

UNITED STATES PATENT AND TRADEMARK OFFICE
CERTIFICATE OF CORRECTION

PATENT NO. : 4,915,685

DATED : April 10, 1990

INVENTOR(S) : TOMASZ J. PETELENZ et al.

It is certified that error appears in the above-identified patent and that said Letters Patent is hereby corrected as shown below:

```
Column 1, line 39, "ha" should be --has--
Column 2, line 57, "toxicity" should be --toxicity.--
Column 2, line 63, "has" should be --have--
Column 3, line 40, "patient s" should be --patient's--
Column 4, line 12, "most of other ions," should be --most of the
other ions--
Column 4, line 18, "pH has" should be --pH have--
Column 10, line 47, "a ion" should be --an ion--
Column 11, line 27, "he resin" should be --the resin--
Column 12, line 52, "H3O" should be --$H^+$--
Column 15, line 49, "the electrode" should be --The electrode--
Column 16, line 5, "resin" should be --resin.--
Column 16, line 14, "is placed" should be --and is placed--
```

Signed and Sealed this

Seventh Day of July, 1992

*Attest:*

DOUGLAS B. COMER

*Attesting Officer*   Acting Commissioner of Patents and Trademarks